(12) United States Patent
Almada

(10) Patent No.: US 6,759,063 B2
(45) Date of Patent: Jul. 6, 2004

(54) METHODS AND COMPOSITIONS FOR REDUCING SYMPATHOMIMETIC-INDUCED SIDE EFFECTS

(76) Inventor: Anthony L. Almada, 1840 41$^{st}$ Ave., Suite 102-227, Capitola, CA (US) 95010

( * ) Notice: Subject to any disclaimer, the term of this patent is extended or adjusted under 35 U.S.C. 154(b) by 0 days.

(21) Appl. No.: 10/044,645

(22) Filed: Jan. 10, 2002

(65) Prior Publication Data

US 2002/0168428 A1 Nov. 14, 2002

Related U.S. Application Data

(63) Continuation-in-part of application No. 09/672,109, filed on Sep. 27, 2000, now abandoned, and a continuation-in-part of application No. PCT/US00/26752, filed on Sep. 27, 2000.
(60) Provisional application No. 60/156,262, filed on Sep. 27, 1999.

(51) Int. Cl.$^7$ .............................................. A61K 35/78
(52) U.S. Cl. ........................ 424/727; 424/725; 424/736
(58) Field of Search ................................ 424/725, 727, 424/736

(56) References Cited

U.S. PATENT DOCUMENTS

| | | | |
|---|---|---|---|
| 5,055,460 | A | 10/1991 | Friedlander |
| 5,284,873 | A | 2/1994 | Salinero-Rodero et al. |
| 6,039,950 | A | 3/2000 | Khwaja et al. |
| 6,200,573 | B1 | 3/2001 | Locke |
| 6,207,694 | B1 * | 3/2001 | Murad |
| 2002/0127189 | A1 * | 9/2002 | Myers et al. |

FOREIGN PATENT DOCUMENTS

| | | |
|---|---|---|
| EP | 0 250 953 B1 | 1/1988 |
| FR | 2 480 754 | 6/1983 |

OTHER PUBLICATIONS

Peirce, A. Am. 1999. Pharm. Assoc. Practical Guide to Natural Medicines, p. 579. William Morrow and Co., Inc. NY, NY.*

Astrup, A. and Toubro S. (1993). "Thermogenic, metabolic, and cardiovascular responses to ephedrine and caffeine in man" *Int. J. Obes. Relat. Metab. Disord.* 17 (Suppl. 1):S41–S43.

Astrup, Arne et al. (1992). "The effect and safety of an ephedrine/caffeine compound compared to ephedrine, caffeine and placebo in obese subjects on an energy restricted diet. A double blind trial" *Int. J. Obes. Relat. Metab. Disord.* 16:269–277.

Breum, Leif et al. (1994). "Comparison of an ephedrine/caffeine combination and dexfenfluramine in the treatment of obesity. A double–blind multi–centre trial in general practice" *Int. J. Obes. Relat. Metab. Disord.* 18:99–103.

Docherty, James R. and Starke, Klaus (1981). "Postsynaptic alpha–adrenoceptor subtypes in rabbit blood vessels and rat anococcygeus muscle studied in vitro" *J. Cardiovasc. Pharmacol.* 3(4): 854–866.

Goepel, Mark et al. (1999). "Saw palmetto extracts potently and noncompetitively inhibit human alpha$_1$–adrenoceptors in vitro" *The Prostate* 38:208–215.

Gurley, Bill J. et al. (1998). "Ephedrine pharmacokinetics after the ingestion of nutritional supplements containing *Ephedra sinica* (ma huang)" *Ther. Drug Monit.* 20:439–445.

Gutierrez M. et al. (1996). "Mechanisms involved in the spasmolytic effect of extracts from *Sabal serrulta* fruit on smooth muscle" *General Pharmacology* 27(1):171–176.

Hamed, A.T. et al. (1983). "Pharmacological characterization of alpha–adrenoreceptor subtypes in rat isolated thoracic aorta" *J. Auton. Pharmacol.* 3:265–273.

Langer, S.Z. and Hicks, P.E. (1984). "Alpha–adrenoreceptor subtypes in blood vessels: physiology and pharmacology" *J. Cardiovasc. Pharmaco.* 6 (Suppl. 4):S547–558.

Lasagna, Louis (1988). *Phenylpropanolamine. A Review* John Wiley & Sons, Table of Contents, pp. IX–XV.

Malchow–Møller, Axel et al. (1981). "Ephedrine as an anorectic: the story of the 'Elsinore pill'" *Int. J. Obes.* 5:183–187.

Morb. Mortal. Wkly. Rep. (1996). "Adverse events associated with ephedrine–containing products—Texas, Dec. 1993–Sep. 1995" 45(32):689–693.

Nadir, Abdul et al. (1996). "Acute hepatitis associated with the use of a Chinese herbal product, Ma–huang" *Am. J. Gastroenterol.* 91(7):1436–1438.

Nasser, J.A. et al. (1999). "Efficacy trial for weight loss of an herbal supplement of Ma Huang and Guarana" *FASEB J.* 13(5):A874, Abstract No. 660.8.

Pasquali, R. et al. (1985). "A controlled trial using ephedrine in the treatment of obesity" *Int. J. Obes.* 9:93–98.

Powell, Thomas et al. (1998). "Ma–Huang strikes again: ephedrine nephrolithiasis" *Am. J. Kidney Dis.* 32(1):153–159.

(List continued on next page.)

*Primary Examiner*—Christopher R. Tate
(74) *Attorney, Agent, or Firm*—King & Spalding, LLP

(57) ABSTRACT

Provided are compositions including *Serenoa repens* and extracts thereof, in combination with a sympathomimetic agent, which may be used to control a variety of physical conditions, including obesity, appetite suppression, decongestion, asthma and energy stimulation. *Serenoa repens*, or extracts thereof, when added to dosage forms of pharmacologic agents with sympathomimetic activity, or when administered in combination with sympathomimetic agents, decreases side effects. Thus, debilitating side effects associated with use of pharmacologic agents that stimulate adrenergic receptors and display sympathomimetic effects can be reduced.

23 Claims, No Drawings

OTHER PUBLICATIONS

Product Allert Bulletin Abstract. (Dec. 21, 1992). "Herbal Bio–Therapy Nutritional Formula for Men."

Product Allert Bulletin Abstract. (Jul. 22, 1996). "Max Dietary Supplement and Plan."

Turek, P.J. et al. Department of Urology, University of California, San Francisco, CA. (1996). "An in vivo microsurgical animal model of seminal vesicle contractility: the effects of alpha–adrenergic agents" *Annual Meeting of the American Society of Reproductive Medicine* pp. S195–S196, Abstract No. P–222.

White, Laura M. et al. (1997). "Pharmacokinetics and cardiovascular effects of Ma–Huang (*Ephedra sinica*) in normotensive adults" *J. Clin. Pharmacol.* 37:116–122.

Zaacks, Stephen M. et al. (1999). "Hypersensitivity myocarditis associated with ephedra use" *J. Toxicol. Clin. Toxicol.* 37(4):485–489.

* cited by examiner

METHODS AND COMPOSITIONS FOR REDUCING SYMPATHOMIMETIC-INDUCED SIDE EFFECTS

This application is a continuation-in-part of U.S. Ser. No. 09/672,109, filed Sep. 27, 2000, now abandoned, which claims the benefit of U.S. Provisional Application Ser. No. 60/156,262, filed Sep. 27, 1999, the disclosures of which are incorporated herein by reference in their entirety. This application also is a continuation of PCT/US00/26752, filed Sep. 27, 2000, which claims the benefit of the disclosures of which are incorporated herein by reference in their entirety.

TECHNICAL FIELD

The present invention relates to compositions containing *Serenoa repens* for formulation in drug, cosmetic, food, and dietary supplements. The present invention relates to compositions comprising *Serenoa repens* and agents with undesired sympathomimetic activity and the use thereof, in clinical or veterinary applications. The present invention relates to reducing the debilitating, untoward and undesirable side effects associated with use of agents that stimulate adrenergic receptors or display sympathomimetic activity.

BACKGROUND ART

Throughout this application, various publications, patents, and published patent applications are referred to by an identifying citation; full citations for these documents may be found at the end of the specification. The disclosure of the publications, patents, and published patent specifications referred in this application are hereby incorporated by reference into the present disclosure.

Sympathomimetic agents are widely used as pharmacologic agents to control or modulate a variety of physical conditions, including obesity, appetite, sinus congestion, body temperature, thermotolerance, asthma, alertness and physical performance. Examples of sympathomimetic agents are mixtures composed of caffeine and ephedrine, and/or its related alkaloids, over the counter ephedrine drugs, phenylpropanolamine, extracts and concentrates of Ephedra species and *Sida cordifolia*, (plant sources of ephedrine and its related alkaloids), norephedrine (phenylpropanolamine) and pseudoephedrine, and synephrine (either synthetic or derived from plant sources). Commonly, use of these pharmacologic agents is accompanied by undesirable, and often debilitating, side effects. Onset of the adverse side effects can result from both direct stimulation of adrenergic receptor activity, primarily alpha-adrenergic receptor activity, and release of neuronal norepinephrine. See, Lasagno, L. "Phenylpropanolamine. A Review" (1988) John Wiley & Sons, Inc. New formulations of the pharmacologic agents delivering pharmacologically equivalent effects with a mitigation of sympathomimetic effects would be a tremendous improvement over the products presently available.

The sympathomimetic agent ephedrine has potent thermogenic and anti-obesity properties in both rodents and humans. The effect is markedly enhanced by caffeine, while caffeine alone has no effect. Astrup et a. (1992) *Int. J. Obes. Relat. Metab. Disord.* 16:269. Reported side effects included tremors, insomnia and dizziness.

Despite its therapeutic efficacy, ephedrine and caffeine (EC) administered in clinically relevant doses produces acute cardiovascular effects. Astrup et al. (1993) *Int. J Obes. Relat. Metab. Disord.* 1:S41–3. EC exerts a supra-additive synergism on thermogenesis and systolic blood pressure, without affecting diastolic blood pressure. EC also increases plasma glucose, insulin and C-peptide concentrations. During dietary energy restriction, EC promotes fat loss and preserves fat-free mass, which may contribute to its chronic effect on energy balance. EC also possesses repartitioning properties, which may be useful in the treatment of obesity. During chronic treatment, the effect of EC on energy expenditure is maintained, while side effects subside after tolerance develops to the hemodynamic and metabolic effects.

In separate studies, dexfenfluramine (DF) and EC have been shown to promote weight loss in obese patients. Breum et al. (1994) *Int. J Obes. Relat. Metab. Disord.* 18:99. Reported side effects included central nervous system side effects, especially agitation, and gastrointestinal symptoms.

A controlled, clinical study comparing the effects of two anorectic drugs, a prescription containing EC (Elsinore pills) and diethylpropion, with placebo was conducted among obese patients, age 18–60 years and overweight 20–80%. Malchow-Moller et al. (1981) *Int. J Obes.* 5:183. Four patients treated with diethylpropion, and four patients treated with EC pills were withdrawn because of complaints of exaltation, tremor and insomnia.

In order to assess the effects of ephedrine hydrochloride on weight loss, a double-blind controlled study was performed in unselected obese outpatients. Pasquali et al. (1985) *Int. J. Obes.* 9:93. Patients receiving ephedrine (150 mg/day) suffered from significantly greater adverse side effects than the placebo group. Ephedrine-containing products derived from various sources are popular for multiple uses, including asthma, weight loss/appetite suppression, energy, enhanced physical performance, sexual enhancement, and euphoria. It would be useful to reduce unwanted side effects of ephedrine containing products.

A double-blind, placebo-controlled 8-week trial was conducted for an herbal supplement containing ma huang (Ephedra: as a source of ephedrine) and guarana as a source of caffeine (Metabolife 356™). Nasser et al. (1999) FASEB J. 13:660.7. Of 67 randomized subjects, 7 dropped out of the study before first follow-up. Of these 7 subjects, 5 were taking the supplement, 1 of which developed high blood pressure and 4 of which reported heart palpitations. Of the 60 subjects who returned for at least one follow-up visit, 12 dropped out of the study before week 8. Of these 12, subjects 6 were taking the supplement, 2 of which reported heart palpitations, 1 of which reported irritability and 1 of which developed increased systolic blood pressure. In subjects who completed the study, increases in the following were reported (supplement versus placebo): dry mouth (5 vs 1); heart palpitations (2 vs 2); blood pressure (>20 pts): systolic (2 vs 0), diastolic (1 vs 1); insomnia (9 vs 2); constipation (1 vs 4) and extra-menstrual bleeding (1 vs 2). This study concluded that this herbal supplement promotes weight loss but may also produce undesirable side effects in some subjects and recommended that long term use would require further study.

In order to evaluate the pharmacokinetic properties of a commercially available source of ephedrine contained in an extract of ma huang, heart rate and blood pressure responses to the product were examined in normotensive, healthy adults. White et al. (1997) *J. Clin. Pharmacol.* 37:116. Ma haung had variable effects on blood pressure and increased heart rate in healthy, normotensive adults.

Ephedrine has previously been described as a causative factor of vasculitis but myocarditis has only recently been associated with either ephedrine or its plant derivative Ephedra. Evidence of this is provided in a case study where a 39-year-old African American male presented with hypertension and a 1-month history of progressive dyspnea on exertion, orthopnea, and dependent edema. Zaacks et al. (1999) *J Toxicol. Clin. Toxicol.* 37:485. He was taking ma huang (Herbalife) 1–3 tablets twice daily for 3 months along with other vitamin supplements, pravastatin, and furosemide. Physical examination revealed that the patient was in mild respiratory distress. Cardiac catheterization with coronary angiography revealed normal coronary arteries, a dilated left ventricle, moderate pulmonary hypertension, and a pulmonary capillary wedge pressure of 34 mm Hg. The patient had right ventricular biopsy performed demonstrating mild myocyte hypertrophy and an infiltrate consisting predominantly of lymphocytes with eosinophils present in significantly increased numbers. Treatment for myocarditis was initiated and one month into therapy, an echocardiogram demonstrated improved left ventricular function with only mild global hypokinesis. A repeat right ventricular biopsy 2 months after the first admission showed no evidence of myocarditis. At 6 months, left ventricular ejection fraction was normal and the patient asymptomatic. Ma huang was the suspected cause of hypersensitivity myocarditis in this patient due to the temporal course of disease and its propensity to induce vasculitis.

Between December 1993 and September 1995, the Bureau of Food and Drug Safety, Texas Department of Health (TDH), received approximately 500 reports of adverse events in persons who consumed dietary supplement products containing ephedrine and associated alkaloids (pseudoephedrine, norephedrine, and N-methyl ephedrine). *Morb. Mortal. Wkly. Rep.* (1996) 45:689. This total included reports by individuals and reports identified by the Bureau of Epidemiology, TDH, in a review of records from the six centers of the Texas Poison Center Network. Adverse effects ranged in severity from tremor and headache to death in eight ephedrine users and included reports of stroke, myocardial infarction, chest pain, seizures, insomnia, nausea and vomiting, fatigue, and dizziness. Seven of the eight reported fatalities were attributed to myocardial infarction or cerebrovascular accident. Although the reports lack sufficient information to unequivocally assign causality, they suggest potential health risks may accompany the use of products containing ephedrine.

Gutierrez M et al. (1996) describe assays of smooth muscle relaxing action of two extracts (total lipid [L] and saponifiable [S]) from *Sabal serrulata* (also known as *Sernoa repens*) fruits on smooth muscle contractions. Both extracts (0.1–1 mg/ml) relaxed the tonic contraction induced by norepinephrine (30 nM) on rat aorta and by KCl (60 mM) on rat uterus. The Sabal extracts (0.3–1 mg/ml) also antagonized the dose-response curve of contractions induced by acetylcholine (0.1–100 microM) on urinary bladder. dL-Propranolol (1 microM) but not the inactive (R)-(+)-propranolol (1 microM) potentiated the Sabal extracts relaxant effect by lowering the EC50. Cycloheximide (10 micrograms/ml) antagonized the effect of extracts from Sabal. However, actinomycin D (5 micrograms/ml) significantly antagonized the effect of the total lipidic extract without modifying that of the saponifiable extract. The relaxant effect of both extracts was not modified by the tyrosine kinase inhibitor genistein (10 microM) or the ornithine decarboxylase inhibitor alpha-difluoromethyl-ornithine (10 mM).

U.S. Pat. No. 5,284,873 discloses obtaining a total acid fraction obtained by alkali hydrolysis of lipid extracts of the fruit of *Sabal serrulata*, which were disclosed as having adrenergic antagonist action and antiinflammatory action, and useful in combatting prostate affections, in particular, benign hypertrophy of the prostate.

*Serenoa repens* extracts are sold in numerous countries as lipid extracts, available in liquid or powder forms, and contain an array of fatty acids such as those described in U.S. Pat. No. 5,284,873. Commercially available *Sereno repens* products include ProstaMed™ (Enzymatic Therapy, Green Bay, Wis.); and Saw Palmetto Extract (Nutrilite, Buena Park, Calif.). Extracts of *Serenoa repens* berries that are commercially available include SabalSelect™ (Indena, Seattle, Wash.); and standardized saw palmetto extract (Euromed, Pittsburgh, Pa.).

U.S. Pat. No. 6,039,950 relates to the use of compositional and activity fingerprints in processing of saw palmetto (also known as *Serenoa repens*) materials to produce drugs for the treatment of diseases.

Goepel, M. et al. (1999) evaluated the alpha 1-adrenoceptor antagonistic properties of various plant-derived compounds and extracts in vitro. Preparations of beta-sitosterol and extracts of stinging nettle, medicinal pumpkin, and saw palmetto were obtained from several pharmaceutical companies. They were tested for their ability to inhibit [3H]tamsulosin binding to human prostatic alpha1-adrenoceptors and [3H]prazosin binding to cloned human alpha1A- and alpha1B-adrenoceptors. Inhibition of phenylephrine-stimulated [3H]inositol phosphate formation by cloned receptors was also investigated. Up to the highest concentration that could be tested, preparations of beta-sitosterol, stinging nettle, and medicinal pumpkin were without consistent inhibitory effect in all assays. In contrast, all tested saw palmetto extracts inhibited radioligand binding to human alpha1-adrenoceptors and agonist-induced [3H]inositol phosphate formation. Saturation binding experiments in the presence of a single saw palmetto extract concentration indicated a noncompetitive antagonism. The relationship between active concentrations in vitro and recommended therapeutic doses for the saw palmetto extracts was slightly lower than that for several chemically defined alpha1-adrenoceptor antagonists. The authors concluded that saw palmetto extracts have alpha1-adrenoceptor-inhibitory properties. Thus, extracts of *Serenoa repens* were demonstrated to be capable of exerting anti-adrenergic effects.

SUMMARY OF THE INVENTION

Provided are compositions comprising *Serenoa repens* or an extract thereof and a sympathomimetic agent. In one embodiment, the *Serenoa repens* or extract thereof has anti-adrenergic activity, and the anti-adrenergic activity is, for example, inhibition of the adverse sympathomimetic effects of the sympathomimetic agent, wherein the adverse effects result, for example, from the effects of the sympathomimetic agent on the alpha-adrenergic receptor.

Optionally, the composition is provided in a pharmaceutically acceptable form. The composition optionally may comprise an extract of *Serenoa repens* comprising, for example, fatty acids or esters thereof, sterols and/or alcohols isolated from *Serenoa repens*. The sympathomimetic agent can be, for example, ephedrine or an ephedrine related alkaloid, alone or in combination with caffeine. Other sympathomimetic agents include synephrine, pseudoephedrine, and phenylpropanolamine.

The sympathomimetic agent also may comprise ma huang or other natural sources of ephedrine or ephedrine related alkaloids, or *Citrus aurantium* or other natural sources of synephrine, or extracts thereof. The term "ephedrine related alkaloid" refers to alkaloids known in the art to have similar structure and the same sympathomimetic activity as ephedrine, such as norephedrine, and pseudoephedrine.

In a further embodiment, there are provided methods of alleviating the side effects of a sympathomimetic agent, comprising administering *Serenoa repens* or an extract thereof, in combination with the sympathomimetic agent, to a human or animal in need thereof. The *Serenoa repens* or extract thereof and the sympthomimetic agent are administered, for example, concomitantly, or within 1–10 minutes, within 1–60 minutes, within 1–4 hours, within 1–6 hours, within 1–24 hours or within 1–48 hours of each other. Optionally, the *Serenoa repens* or extract thereof is administered prior to or after the sympathomimetic agent. Optionally, the *Serenoa repens* or extract thereof is administered in an amount effective to reduce side effects, for example due to agonistic adrenergic receptor activity of the sympathomimetic agent.

In the method, the *Serenoa repens* or extract thereof optionally has anti-adrenergic activity. For example, the *Serenoa repens* may inhibit the effect of the sympathomimetic agent on the alpha-adrenergic receptor, such as binding of the sympathomimetic agent to the alpha-adrenergic receptor. The *Serenoa repens* or extract thereof, and the sympathomimetic agent may be administered in a pharmaceutically acceptable form. The method may comprise administering an extract of *Serenoa repens* comprising, for example, fatty acids or esters thereof, sterols and/or alcohols isolated from *Serenoa repens*.

MODES FOR CARRYING OUT THE INVENTION

The invention encompasses a composition comprising *Serenoa repens* or extract thereof and a sympathomimetic agent. Optionally, the *Serenoa repens* or extract thereof is present in an amount effective to inhibit adverse sympathomimetic effects of the sympathomimetic agent, such as binding or other effect of the sympathomimetic agent on the alpha-adrenergic receptor, upon administration. The adrenergic activity inhibited by the *Serenoa repens* or extract thereof can be inhibition of agonistic binding of the sympathomimetic agent to the alpha-adrenergic receptor. The invention further encompasses a composition comprising *Serenoa repens* or extract thereof and a pharmacologic agent having sympathomimetic activity.

The pharmacologic agents having sympathomimetic activity include but are not limited to ephedrine and its related alkaloids, mixtures of ephedrine (and/or its related alkaloids) and caffeine, over the counter ephedrine, synephrine, pseudoephedrine, or phenylpropanolamine drugs, ma huang or other natural sources of ephedrine and its related alkaloids, *Citrus aurantium* or other natural sources of synephrine. The *Serenoa repens* or extract thereof optionally is present in an amount sufficient to decrease the side effects of pharmacologic agents having sympathomimetic activity.

The *Serenoa repens* or extract thereof is obtained by standard botanical processing methods known in the art. Decrease of the sympathomimetic side effects is measured by methods known in the art.

Sympathomimetic agents that can be used in the compositions and methods disclosed herein include a wide variety of agents used as pharmacologic agents to control or modulate a variety of physical conditions, including obesity, appetite, sinus congestion, body temperature, thermotolerance, asthma, alertness and physical performance. Examples of sympathomimetic agents include ephedrine, caffeine/ephedrine mixtures, and/or related ephedrine alkaloids, over the counter ephedrine drugs, phenylpropanolamine, extracts and concentrates of Ephedra species and *Sida cordifolia*, (plant sources of ephedrine and its related alkaloids), norephedrine (phenylpropanolamine), pseudoephedrine, and synephrine (either synthetic or derived from plant sources), and combinations thereof.

The *Serenoa repens* or extract thereof can be provided in a composition with the symphathomimetic agent, or administered in combination with the sympathomimetic agent. In one embodiment, the *Serenoa repens* or extract thereof is present in the composition, or is administered, in an amount effective to reduce undesirable side effects of the sympathomimetic agent. Without being limited to any theories, it is believed that the side effects can be reduced by such pathways as reducing direct stimulation of adrenergic receptor activity, primarily alpha-adrenergic receptor activity, and release of neuronal norepinephrine. For example, 25–5,000 mg, or e.g., 50–1000 mg, or 50–500 mg of *Serenoa repens* or extract thereof can be administered or be present in a dosage amount in a composition for administration to a mammal, such as a human.

In one embodiment, ephedrine, alone or in combination with caffeine, is provided in a composition with *Serenoa repens* or extract thereof, or is administered in combination with *Serenoa repens* or extract thereof, in order to provide, for example, thermogenic and anti-obesity effects. For example, the composition in one embodiment comprises 5–50 mg ephedrine, 5–500 mg caffeine and 25–5,000 mg of *Serenoa repens* or extract thereof.

Thus, the dosage amount of the sympathomimetic agent in the composition can vary between about 5–5,000 mg, for example, between 5–500 mg, or between 5–100 mg or 5–50 mg. For example, 5–50 mg ephedrine, 5–500 mg caffeine, 5–100 mg synephrine, 5–75 mg pseudoephedrine or 5–100 mg phenylpropanolamine drugs or combinations thereof can be used.

In another embodiment, *Serenoa repens* or extract thereof is provided in a composition together with, or is administered in combination with an herbal supplement containing Ephedra or *Sida cordifolia* as a source of ephedrine and guarana (for example, Metabolife 356™, San Diego, Calif.), black tea, oolong tea, green tea, coffee or cola as a source of caffeine.

Serenoa repens

*Serenoa repens* (also known as *Sabal serrulata*) and extracts are commercially available. Commercially available *Serenoa repens* products include ProstaMed™ (Enzymatic Therapy, Green Bay, Wis.); and Saw Palmetto Extract (Nutrilite, Buena Park, Calif.). Extracts of *Serenoa repens* berries are commercially available including SabalSelect™ (Indena, Seattle, Wash.); and standardized saw palmetto extract (Euromed, Pittsburgh, Pa.).

As used herein, the term "*Serenoa repens* extracts" refers to products and fractions that have been derived from *Serenoa repens*, for example from the fruit thereof. Methods of processing *Serenoa repens* have been described in the art. For example, Gutierrez et al. (1996) describe the isolation of two extracts (total lipid [L] and saponifiable [S]) from *Sabal serrulata* fruits.

U.S. Pat. No. 6,039,950 describes methods of obtaining extracts of saw palmetto wherein raw material is processed and assayed at different stages of processing. Processing methods include extraction and precipitation.

Goepel, M. et al. (1999) discloses saw palmetto materials obtained from commercially available sources, which may be used in accordance with the present invention.

The activity of *Serenoa repens* and extracts thereof on alpha-adrenoreceptor subtypes can be measured as described in the art. See, e.g., Docherty et al., "Postsynaptic alpha-adrenoceptor subtypes in rabbit blood vessels and rat anococcygeus muscle studied in vitro," *J. Cardiovasc. Pharmacol.* 3(4): 854–66, 1981. Postsynaptic alpha-adrenoceptor subtypes are investigated in vitro, employing rabbit aorta, pulmonary artery, and portal vein, and rat anococcygeus. In this study, phenylephrine (alpha 1-selective), alpha-methylnoradrenaline (mixed agonist), and xylazine (alpha 2-selective) were used as agonists, and prazosin (alpha 1-selective) and rauwolscine (alpha 2-selective) as antagonists.

The activity of *Serenoa repens* and extracts thereof can be measured on alpha-adrenoreceptor subtypes as described in: Langer et al., "Alpha-adrenoreceptor subtypes in blood vessels: physiology and pharmacology," *J Cardiovasc Pharmacol* 6(Suppl 4): S547–58, 1984. For example, two subtypes of alpha-adrenoreceptors as defined by a different profile of affinity and relative order of potencies for agonists and for antagonists can be assayed. For example, in blood vessels, both the alpha 1- and the alpha 2-adrenoreceptor subtypes are present postsynaptically, where they mediate vasoconstriction, although the alpha 1-adrenoreceptor is the predominant receptor in vascular smooth muscle.

Carriers and Administration

The compositions may be administered by a variety of routes known in the art including topical, sublingual, transdermal, oral, parenteral (including intravenous, intraperitoneal, intramuscular and subcutaneous injection as well as intranasal or inhalation administration) and implantation. The compositions may be administered to humans as well as to animals for veterinary purposes.

The compositions may be provided in pharmaceutically acceptable form, and may be provided in a variety of carriers, including a range of pharmaceutically acceptable carriers available in the art. The carriers may include, for example, binders, lubricants, stabilizers, sugars, amino acids, and electrolytes, diluents, solvents, buffers, and solubilizers. The compositions may include a carrier suitable for the particular route of administration selected including topical, oral, parenteral (including intravenous, intraperitoneal, intramuscular and subcutaneous injection as well as intranasal or inhalation administration) and implantation, as described in the art, for example, in "Remington: The Science and Practice of Pharmacy", Mack Publishing Company, Pennsylvania, 1995, the disclosure of which is incorporated herein by reference.

Publications

The disclosures of the publications, patents, and published patent specifications referenced herein are hereby incorporated by reference into the present disclosure in their entirety.

U.S. Pat. No. 5,055,460 (1991)

U.S. Pat. No. 5,284,873 (1994)

U.S. Pat. No. 6,039,950 (2000)

Astrup, A., et al., "The effect and safety of an ephedrine/caffeine compound compared to ephedrine, caffeine and placebo in obese subjects on an energy restricted diet. A double blind trial." *Int. J. Obes. Relat. Metab. Disord.* 16(4): 269–77, 1992.

Astrup, A. et al. "Thermogenic, metabolic and cardiovascular responses to ephedrine and caffeine in man." *Int. J. Obes. Relat. Metab. Disord.* 17(SUPPL 1): S41–S43, 1993.

Breum, L., et al. "Comparison of an ephedrine/caffeine combination and dexfenfluramine in the treatment of obesity. A double-blind multi-centre trial in general practice." *Int. J. Obes. Relat. Metab. Disord.* 18(2): 99–103, 1994.

Goepel, M., U. Hecker, et al. "Saw palmetto extracts potently and noncompetitively inhibit human alpha1-adrenoceptors in vitro." *Prostate* 38(3): 208–15, 1999.

Gutierrez, M., M. J. Garcia de Boto, et al. "Mechanisms involved in the spasmolytic effect of extracts from Sabal serrulata fruit on smooth muscle." *Gen Pharmacol* 27(1): 171–6, 1996.

Malchow-Moller, A., et al. "Ephedrine as an anorectic: the story of the 'Elsinore pill'." *Int. J. Obes.* 5(2): 183–7, 1981.

Centers For Disease Control. Adverse events associated with ephedrine-containing products: Texas, December 1993–September 1995. *Morbidity and Mortality Weekly Report* 45(32): 689–693, 1996.

Nasser, J. A., et al. "Efficacy trial for weight loss of an herbal supplement of Ma Huang and Guarana." *FASEB J* 13(5 PART 2): A874, 1999.

Pasquali, R. et al. "A controlled trial using ephedrine in the treatment of obesity." *Int. J Obes.* 9(2): 93–8, 1985.

White, L. M., et al. "Pharmacokinetics and cardiovascular effects of ma huang (*Ephedra sinica*) in normotensive adults." *J Clin. Pharmacol.* 37(2): 116–22, 1997.

Zaacks, S. M., et al. "Hypersensitivity myocarditis associated with ephedra use." *J. Toxicol. Clin. Toxicol.* 37(4): 485–489, 1999.

EXAMPLES

Example 1

Activity Assay

The effective concentration of *Serenoa repens* or extract thereof to reduce side effects of sympathomimetic agents is tested using methods available in the art. The amount of *Serenoa repens* or extract thereof used is in one embodiment an effective amount to act as an alpha-adrenoreceptor antagonist.

In one embodiment, a rat model of seminal vesicle contractility is used, wherein seminal vesicle muscular activity is pharmacologically altered by alpha1-adrenergic agents. See "An In Vivo Microsurgical Animal Model of Seminal Vesicle Contractility: The Effects of Alpha-Adrenergic Agents," American Society of Reproductive Medicine, 1996 annual meeting, P. J. Turek, A. K. Younes, K. Aslam. Department of Urology, University of California. San Francisco, Calif.

The in vivo rat model of seminal vesicle contractility employs hypogastric nerve stimulation. In vivo seminal vesicle contractile function is altered by alpha adrenergic agonists and antagonists.

After anesthesia, the seminal vesicle is isolated in Wistar rats and cannulated microsurgically. Seminal vesicle luminal pressures are transduced and recorded. Central arterial and venous lines are established. After hypogastric nerve stimulation with a microelectrode, a biphasic pressure response is measured as twitch (height, mm) and secondary (area under curve) phases. A repetitive nerve stimulation study is performed to assess reproducibility. Additionally, the effect of the alpha1-adrenergic agents *Serenoa repens* or extract thereof (antagonist) and a sympathomimetic agent (agonist) on SV contractility is examined by infusing for example 1.0 mg/kg *Serenoa repens* or extract thereof and then for example 1.25 mg/kg sympathomimetic agent after an initial control stimulation. SV contractile pressures are measured after each drug is infused and expressed as percent of the control stimulation. Mean responses and measures of variance are calculated.

Reproducible seminal vesicle contractile responses with stimulations at >10 minute intervals can be obtained. Alpha1-adrenergic blockade from the *Serenoa repens* or extract thereof results in a statistically significant decrease in seminal vesicle contraction pressures. The effect of the sympathomimetic agent alone and with pre or co-administration of the *Serenoa repens* or extract thereof is compared to determine the effective concentration of *Serenoa repens* or extract thereof to reduce the stimulation of the alpha1-adrenergic receptor by the sympathomimetic agent.

Example 2

Activity Assay

The effective concentration of *Serenoa repens* or extract thereof to reduce side effects of sympathomimetic agents is tested using methods available in the art. The amount of *Serenoa repens* or extract thereof used is in one embodiment an effective amount to act as an alpha-adrenoreceptor antagonist.

Alpha-adrenoreceptor mediated contraction in rat isolated thoracic aorta is measured, as described in Hamed et al. "Pharmacological characterization of alpha-adrenoreceptor subtypes in rat isolated thoracic aorta," *J Auton Pharmacol* 3(4): 265–73, 1983. The alpha-adrenoreceptor mediated contraction in rat isolated thoracic aorta is measured using agonist (sympathomimetic agent) and antagonists (*Serenoa repens* or extract thereof), and by utilizing mixed agonist and antagonist interactions.

Example 3

Activity Assay

The effective concentration of *Serenoa repens* or an extract thereof to reduce side effects of sympathomimetic agents is tested using methods available in the art. The amount of *Serenoa repens* or extract thereof used is in one embodiment an effective amount to act as an alpha-adrenoreceptor antagonist.

*Serenoa repens* or an extract thereof, used as an alpha-adrenoreceptor blocking agent, is used as administered to patients prior to or contemporaneously with administration of a sympathomimetic agent. Blood pressure and heart rate are measured continuously over prolonged ambulatory periods for example using an established invasive technique before and after administration. The protocol is randomised, double-blind, and double-dummy placebo controlled. A standardized program of physiological stress testing also is performed during each study. Change in the levels or patterns of blood pressure over 24-h periods, and physiological testing for side effects such as hypotension, and the response to dynamic and isometric exercise is examined to determine the effect of the *Serenoa repens* or extract thereof on reduction of side effects caused by the sympathomimetic agent, such as agitation, gastrointestinal symptoms, insomnia, hypertension, heart palpitations, irritability, hyperglycemia, dry mouth, blood pressure, systolic, diastolic, constipation and extra-menstrual bleeding.

Example 4

Production of *Serenoa repens* Extracts

Extracts of the fruits of *Serenoa repens* are produced as described in European Patent 492 305. An extract of *Serenoa repens* is produced using ethanol or hexane as solvents to treat a maceration of the fruits. Product fractions are obtained using methods available in the art such as crystallization and chromatography. Another embodiment of obtaining an extract is described in French Patent No. 2 480 754, wherein *Serenoa repens* material is treated with polar solvents in the presence of anti-oxidants in an inert atmosphere. Active fractions are characterized as described herein and may be further purified using methods available in the art. Another method of obtaining an extract of *Serenoa repens* is described in European Patent No. 0 250 953, wherein carbon dioxide is used as the solvent under high pressure conditions, for example, at pressures ranging from 100 to 350 bars and at temperatures ranging from 30 degrees Centigrade to 50 degrees Centigrade. Active fractions are identified using assays described herein and available in the art, and may be further purified by methods available in the art.

What is claimed is:

1. A composition comprising *Serenoa repens* or an extract thereof and a sympathomimetic agent, wherein the sympathomimetic agent is synephrine, wherein the composition is suitable for oral administration.

2. The composition of claim 1, wherein the *Serenoa repens* or extract thereof has anti-adrenergic activity.

3. The composition of claim 2, wherein the anti-adrenergic activity is inhibition of agonist binding to the alpha-adrenergic receptor.

4. The composition of claim 1, wherein the composition is in a pharmaceutically acceptable form.

5. A composition comprising *Serenoa repens* or an extract thereof and a sympathomimetic agent, wherein the sympathomimetic agent is an extract of *Citrus aurantium* containing synephrine therein or other natural source of synephrine, wherein the composition is suitable for oral administration.

6. The composition of claim 5, wherein the *Serenoa repens* or extract thereof has anti-adrenergic activity.

7. The composition of claim 6, wherein the anti-adrenergic activity is inhibition of agonist binding the alpha-adrenergic receptor.

8. The composition of claim 5, wherein the *Serenoa repens* or extract thereof is administered in a pharmaceutically acceptable form.

9. A method of alleviating the aide effects of a sympathomimetic agent, the method comprising administering *Serenoa repens* or extract thereof, and a sympathomimetic agent, to a human or animal in need thereof;
   wherein the *Serenoa repens* or extract thereof is administered in an amount effective to reduce side effects of the sympathomimetic agent.

10. The method of claim 9, wherein the *Serenoa repens* or extract thereof has anti-adrenergic activity.

11. The method of claim 10, wherein the anti-adrenergic activity is inhibition of agonist binding the alpha-adrenergic receptor.

12. The method of claim 9, wherein the *Serenoa repens* or extract thereof is administered in a pharmaceutically acceptable form.

13. The method of claim 9, where the sympathomimetic agent comprises ephedrine or an ephedrine related alkaloid.

14. The method of claim 9, where the sympathomimetic agent comprises a mixture of ephedrine or ephedrine related alkaloid and caffeine.

15. The method of claim 9, where the sympathomimetic agent is selected from the group consisting of synephrine, pseudoephedrine and phenylpropanolamine.

16. The method of claim 9, wherein the sympathomimetic agent is ma huang or other natural sources of ephedrine or related alkaloids, or an extract of *Citrus aurantium* containing synephrine therein or other natural source of synephrine.

17. The method of claim 9, wherein the *Serenoa repens* or extract thereof is administered at least 24 hours prior to administration of the sympathomimetic agent.

18. The method of claim 17, wherein the *Serenoa repens* or extract thereof and the sympathomimetic agent are administered by a route selected from the group consisting of topical, sublingual, transdermal, oral, parenteral and implantation.

19. The method of claim 9, wherein the *Serenoa repens* or extract thereof and the sympathomimetic agent are administered by a route selected from the group consisting of topical, sublingual, transdermal, oral, parenteral and implantation.

20. A composition comprising *Serenoa repens* or an extract thereof and a sympathomimetic agent, wherein the sympathomimetic agent is an extract of *Citrus aurantium* containing synephrine therein, or other natural source of synephrine wherein the sympathomimetic agent is at a concentration between 5–5,000, and wherein the composition is suitable for oral administration.

21. The composition of claim 20, wherein the *Serenoa repens* or extract thereof has anti-adrenergic activity.

22. The composition of claim 21, wherein the anti-adrenergic activity is inhibition of agonist binding to the alpha-adrenergic receptor.

23. The composition of claim 20, wherein the composition is in a pharmaceutically acceptable form.

* * * * *